(12) United States Patent
Ciach et al.

(10) Patent No.: US 10,702,633 B2
(45) Date of Patent: Jul. 7, 2020

(54) METHOD OF MANUFACTURING INTRAMEDULLARY NAILS MADE OF CHITOSAN FOR LONG BONES FRACTURES TREATMENT

(71) Applicant: WARSZAWSKI UNIWERSYTET MEDYCZNY, Warsaw (PL)

(72) Inventors: Tomasz Ciach, Warsaw (PL); Jaroslaw Deszczyński, Warsaw (PL); Jaroslaw Michal Deszczyński, Warsaw (PL); Tomasz Mitek, Warsaw (PL); Lukasz Nagraba, Warsaw (PL); Artur Stolarczyk, Józefów (PL)

(73) Assignee: WARSZAWSKI UNIWERSYTET MEDYCZNY, Warsaw (PL)

( * ) Notice: Subject to any disclaimer, the term of this patent is extended or adjusted under 35 U.S.C. 154(b) by 93 days.

(21) Appl. No.: 15/633,036

(22) Filed: Jun. 26, 2017

(65) Prior Publication Data

US 2017/0354766 A1    Dec. 14, 2017

Related U.S. Application Data

(63) Continuation of application No. PCT/PL2014/000099, filed on Sep. 2, 2014.

(30) Foreign Application Priority Data

Aug. 21, 2014   (PL) ..................... P.409231

(51) Int. Cl.
| | |
|---|---|
| *A61L 31/04* | (2006.01) |
| *C08L 5/08* | (2006.01) |
| *A61L 31/14* | (2006.01) |
| *B29C 41/00* | (2006.01) |
| *B29C 41/04* | (2006.01) |
| *C08J 5/00* | (2006.01) |
| *B29K 105/00* | (2006.01) |
| *B29L 31/00* | (2006.01) |

(52) U.S. Cl.
CPC ........... *A61L 31/042* (2013.01); *A61L 31/146* (2013.01); *A61L 31/148* (2013.01); *B29C 41/003* (2013.01); *B29C 41/04* (2013.01); *C08J 5/00* (2013.01); *C08L 5/08* (2013.01); *A61L 2430/02* (2013.01); *B29K 2105/0073* (2013.01); *B29L 2031/7286* (2013.01); *C08J 2305/08* (2013.01)

(58) Field of Classification Search
CPC .... A61L 31/042; A61L 31/146; A61L 31/148; B29C 41/003; B29C 41/04; B29K 2105/0073; C08J 2305/08
See application file for complete search history.

(56) References Cited

U.S. PATENT DOCUMENTS

| | | | | |
|---|---|---|---|---|
| 5,599,916 A | * | 2/1997 | Dutkiewicz | A61L 15/28 536/20 |
| 2008/0254125 A1 | * | 10/2008 | Freier | A61K 9/0024 424/488 |
| 2011/0229432 A1 | * | 9/2011 | Choi | A61L 31/041 424/78.3 |
| 2013/0244972 A1 | * | 9/2013 | Ben-Shalom | C08L 5/08 514/55 |

FOREIGN PATENT DOCUMENTS

WO    WO-2009035413 A1 *  3/2009  ........... C08B 37/003

* cited by examiner

*Primary Examiner* — Joseph S Del Sole
*Assistant Examiner* — Jennifer A Kessie
(74) *Attorney, Agent, or Firm* — Browdy and Neimark, PLLC

(57) ABSTRACT

The method, characterized in that, the powdered chitosan is dissolved in water to obtain a 5% solution, into which a 70-90% acetic acid is added and after the formation of the blank intramedullary nail and carrying a coagulating bath and neutralization bath it is subjected to a crosslinking bath in a solution formed from 0.5 to 2% of sodium tri-polyphosphate and 0.5% to 3% Na3PO4 for 24 to 48 hours in temperature of 50° C. to 140° C. and then it is subjected to the drying process, for a period of 6 to 10 days, and finally the surface of the blank is treated to form the intramedullary nail. The surface treatment is carried out until the surface of the intramedullary nail contains at least 20%-40% of the pore of the depth of 0.1 mm to 1 mm.

2 Claims, No Drawings

METHOD OF MANUFACTURING INTRAMEDULLARY NAILS MADE OF CHITOSAN FOR LONG BONES FRACTURES TREATMENT

The object the invention is the method of manufacturing intramedullary nails made of chitosan for the treatment of long bones fractures.

PL392504 A1 describes the method of manufacturing intramedullary nails, in which pH stabilizing mineral filler, such as calcium carbonate, magnesium oxide, magnesium hydroxide, magnesium carbonate, calcium phosphate and magnesium, calcium phosphate (B-TCP), or mixtures thereof are added to melted polymer, such as polylactide (PLA) or polyglycolide (PGA), or copolymers thereof and then the material is fed to the injection moulding machine in order to manufacture intramedullary nails.

This publication describes also another method of manufacturing intramedullary nails, made of chitosan fibers, obtained by spinning of a solution of water and an acid selected from acetic acid, hydrochloric acid, phosphoric acid. Bundles of fibers are bonded to form a rod by means of pressing at elevated temperature or by immersion in a solution of water and an acid selected from acetic acid, hydrochloric acid, phosphoric acid or in a solution of polylactide (PLA), polyglycolide (PGA) or polycaprolactone (PCP) and an organic solvent, the melted rod which is fed to the injection moulding machine in order to manufacture intramedullary nails.

CN 1352991 A discloses a method of manufacturing material made of chitosan for the manufacture of medical nails or rods, which consists of dissolving the chitosan in 2% acetic acid and coating the inner surface of the mold with this solution, filling the mold with 3-8% NaOH solution, which after forming gel is removed, and such prepared die is filled with said solution of chitosan in acetic acid. After the product is created in the die, it is subjected to neutralization with coagulation solution and then immersed in water until it obtains neutral pH, then the drying process is carried.

The purpose of the invention is to further improve the method of manufacturing intramedullary nails made of chitosan for the treatment of long bone fractures, capable of producing high bending strength and high Young's modulus corresponding to the strength of long bone, while providing the appropriate structure and degree of degradability Surprisingly, we found that the above task can be solved by using 5% aqueous solution of chitosan with the addition of highly concentrated acetic acid.

In detail, the task of the invention is solved by dissolving powdered chitosan in water to obtain a 5% solution, into which a 70-90% acetic acid is added and after the formation of the blank intramedullary nail and carrying a coagulating bath, it is neutralized in deionized water to a pH of 6.5-7.5, and then subjected to a crosslinking bath in a solution formed from 0.5 to 2% of sodium tri-polyphosphate and 0.5% to 3% $Na_3PO_4$ for 24 to 48 hours and in temperature of 50° C. to 140° C. and then subjected to the drying process, for period of 6 to 10 days, and finally the surface of the blank is treated to form the intramedullary nail.

Preferably, the surface treatment is carried out until the surface of the intramedullary nail contains at least 20%-40% of the pore of the depth of 0.1 mm to 1 mm.

The method uses natural chitosan derived from marine organisms having a molecular weight of 200,000 to 10000000 Da, deacetylation degree of 80-98% and grain size of 0.1 mm to 1 mm.

The advantage of the invention is to provide an intramedullary nail, which despite the occurrence of a specified quantity of intentional surface pores, facilitating or accelerating the degradation process of the intramedullary nail in a living body, has a strength comparable to the strength of the long bone. During the process, the blank intramedullary nail can be easily shaped, and its finishing treatment to form the desired shape (dimensions) is problem-free.

EXAMPLE

In the first stage natural chitosan was prepared, obtained in known manner from marine organisms, having a molecular weight of 5000000 Da and deacetylation degree of 90% and grain size of 0.5 mm. Then powdered chitosan was dissolved in the amount of water sufficient to obtain a 5% solution. While this solution was being continuously stirred 80% acetic acid was added and left for 24 hours in order to get rid of existing air bubbles and achieve a homogeneous solution.

In the second stage of the process the mold for the blank intramedullary nail was prepared. For this purpose, cylindrical mold was put into rotation and filled with said 5% aqueous chitosan solution until a uniform coating of 0.4 mm thickness on the inner walls of the mold was obtained. After the formation of the coating the mold was filled with 5% aqueous NaOH solution and left for 10 to 30 minutes to obtain a gel die.

Then, NaOH solution was removed and thus formed die was completely filled with said 5% chitosan solution until the blank intramedullary nail was formed.

In the next step the blank was subjected, during up to 24 hours, to a coagulation bath formed of 5% aqueous solution of NaOH, in order to complete precipitation of chitosan.

Then, the blank was subjected to a bath of deionized water until the water reached pH of 7.0, and then the blank was subjected to cross-linking bath, formed from a solution containing: 1% by weight of sodium tri-polyphosphate and 2% by weight of $Na_3PO_4$, during 34 hours at 50° C., in order to increase the density of the material of the blank (obtained increase in strength of 30 MPa and in the flexural modulus of 1.5 GPa).

The next step was the process of drying the blank carried for 8 days.

The blank thus obtained was subjected to strength tests, namely, the three-point bending test, while the flexural strength (W) and the flexural modulus (E) were examined. Tests have shown respectively W=130 MPa and E=2.6 GPa.

These values are fully sufficient for the blank to be suitable for manufacturing the intramedullary nail, which fulfills the requirements, as these values are only slightly less than the strength of a human long bone.

During drying of the blank, surface irregularities were observed with respect to its diameter and length. It turned out, however, that these irregularities can be successfully removed by carrying out the smoothing surface treatment until 20% of the surface with the pores of at least 0.4 mm is obtained. Studies have shown that the treatment leaving the surface pores with a depth of 0.5 mm is adequate. From carried biodegradation survey it occurs that such pores effectively contribute to reduced biodegradation process living organism.

The biodegradation degree survey was conducted in PBS Ringer's solution having a pH of 7.4, containing 0.1% by weight of sodium nitride at a temperature of 37° C. The survey lasted 5 months up to the complete hydrolysis of chitosan. After the survey, the blank was subjected to a drying process at 70° C., which continued until a constant weight was obtained. After drying, the weight loss was 30%, the diameter was reduced by 20% and the length by 10%.

On the basis of this information, the skilled specialist can easily determine the size of the mold needed for the particular type (size) of the intramedullary nail.

The invention claimed is:

1. A method for manufacturing of intramedullary nails made of chitosan for fracture treatments of long bones, consisting of the following steps:
   a) preparing powdered chitosan, obtained in deacetylation process of chitin from marine organisms;
   b) dissolving the powdered chitosan in water to obtain a 5% chitosan solution into which a 70-90% acetic acid is added, while stirring, until a uniform chitosan solution is obtained;
   c) coating the inner surface of a mold with said uniform chitosan solution and filling the thus formed coated mold with a coagulation bath of 5% aqueous solution of NaOH to obtain a gel die;
   d) removing the coagulation bath from the gel die and filling the gel die with the uniform chitosan solution obtained in step (b), and subsequently subjecting the filled gel die to a coagulation bath of 5% aqueous solution of NaOH and thus forming a blank intramedullary nail in the gel die;
   e) subjecting the blank intramedullary nail obtained in step (d) to a neutralizing bath of deionized water to a pH of 6.5-7.5 after the coagulation bath is removed,
   f) subjecting the blank intramedullary nail obtained in step (e) to a crosslinking bath in a solution formed from 0.5 to 2% of sodium tripolyphosphate and 0.5% to 3% $Na_3PO_4$ for 24 to 48 hours at a temperature of 50° C. to 140° C.;
   g) subjecting the blank intramedullary nail obtained in step (f) to a drying process for a period of 6 to 10 days, thus obtaining a dry blank intramedullary nail having flexural strength (W) of 130 MPa and flexural modulus (E) of 2.6 GPa; and
   h) treating a surface of the dry blank intramedullary nail obtained in step (g) to form an intramedullary nail, wherein the surface treatment is carried out until the surface of the intramedullary nail contains at least 20%-40% of pores having a depth of 0.1 mm to 1 mm.

2. The method according to claim 1, wherein natural chitosan derived from marine organisms used in step (b) has a molecular weight of 200,000 to 10,000,000 Da, deacetylation degree of 80-98% and grain size of 0.1 mm to 1 mm.

* * * * *